(12) United States Patent
Jin et al.

(10) Patent No.: US 11,286,524 B2
(45) Date of Patent: Mar. 29, 2022

(54) MULTI-POSITION DOUBLE-TAG CONNECTOR SET FOR DETECTING GENE MUTATION AND PREPARATION METHOD THEREFOR AND APPLICATION THEREOF

(71) Applicant: AMOY DIAGNOSTICS CO., LTD., Xiamen (CN)

(72) Inventors: Baolei Jin, Xiamen (CN); Xuchao Li, Xiamen (CN); Qinghua Lin, Xiamen (CN); Weijie Shi, Xiamen (CN); Huijuan Ge, Xiamen (CN); Li Ruan, Xiamen (CN)

(73) Assignee: Amoy Diagnostics Co., Ltd., Fujian (CN)

( * ) Notice: Subject to any disclaimer, the term of this patent is extended or adjusted under 35 U.S.C. 154(b) by 387 days.

(21) Appl. No.: 16/322,340

(22) PCT Filed: Aug. 28, 2017

(86) PCT No.: PCT/CN2017/099255
§ 371 (c)(1),
(2) Date: Jan. 31, 2019

(87) PCT Pub. No.: WO2018/041062
PCT Pub. Date: Mar. 8, 2018

(65) Prior Publication Data
US 2020/0010892 A1    Jan. 9, 2020

(30) Foreign Application Priority Data

Aug. 29, 2016 (CN) .......................... 201610754636.4

(51) Int. Cl.
| | | |
|---|---|---|
| *C12Q 1/6876* | (2018.01) | |
| *C12N 15/10* | (2006.01) | |
| *C12Q 1/6806* | (2018.01) | |
| *C12Q 1/6869* | (2018.01) | |

(52) U.S. Cl.
CPC ....... *C12Q 1/6876* (2013.01); *C12N 15/1065* (2013.01); *C12N 15/1068* (2013.01); *C12Q 1/6806* (2013.01); *C12Q 1/6869* (2013.01); *C12Q 2600/156* (2013.01)

(58) Field of Classification Search
None
See application file for complete search history.

(56) References Cited

FOREIGN PATENT DOCUMENTS

| | | |
|---|---|---|
| CN | 101967476 A | 2/2011 |
| CN | 102978205 A | 3/2013 |
| CN | 103667273 A | 3/2014 |
| CN | 103882530 A | 6/2014 |
| CN | 104263726 A | 1/2015 |
| CN | 104313699 A | 1/2015 |
| CN | 104561294 A | 4/2015 |
| CN | 105586427 A | 5/2016 |
| CN | 106086162 A | 11/2016 |
| CN | 106282177 A | 1/2017 |
| CN | 106367485 A | 2/2017 |
| CN | 106893774 A | 6/2017 |
| EP | 3505640 A1 | 7/2019 |
| KR | 101651817 B1 | 8/2016 |
| WO | 0198533 A2 | 12/2001 |
| WO | WO-2007052006 A1 | 5/2007 |
| WO | 2015128272 A2 | 9/2015 |
| WO | 2018041062 A1 | 3/2018 |

OTHER PUBLICATIONS

Schmitt et al., "Detection of ultra-rare mutations by next-generation sequencing," Proc. Natl. Acad. Sci. USA 2012, 109:14508-14513. (Year: 2012).*
NEBNext Multiplex Oligos for Illumina, New England Biolabs, Inc., https://www.neb.com/-/MEDIA/CATALOG/Datacards%20or%20Manuals/manualE7600.pdf, Dec. 31, 2016, entire document.
"Detecting Ultralow-Frequency Mutations by Duplex Sequencing", Oct. 2014, Scott R. Kennedy, Micahel W. Schmitt, Edward J. Fox, Brendan F. Kohrn, Jesse J. Salk, Eun Hyun Ahn, Marc J. Prindle, Kawai J. Kuong, Jiang-Chen Shen, Rosa-Ana Resques and Lawence A. Loeb, Nature Protocols, vol. 9, No. 11, pp. 2586-2606.

* cited by examiner

*Primary Examiner* — Kaijiang Zhang
(74) *Attorney, Agent, or Firm* — Cooper Legal Group, LLC

(57) ABSTRACT

A multi-position double-tag adapter set for detecting gene mutation and preparation method therefor and application thereof, the multi-position double-tag adapter set comprising a double-tag adapter A, a double-tag adapter B and a double-tag adapter C. The double-tag adapter A, the double-tag adapter B and the double-tag adapter C are obtained respectively by hybridizing an adapter primer P5 with an adapter primer P7-A, an adapter primer P7-B and an adapter primer P7-C 5' ends of which are all modified with biotin. Using the multi-position double-tag adapter set, the mutation rate of $1\times10^{-5}$ genes may be accurately detected and the sensitivity of gene mutation detection may be effectively improved. A plurality of mutation sites of a plurality of genes may be detected by one-time sequencing in combination with throughput of high-throughput sequencing.

16 Claims, 6 Drawing Sheets

Specification includes a Sequence Listing.

SEQUENCE LISTING

<160> NUMBER OF SEQ ID NOS: 31

<210> SEQ ID NO 1
<211> LENGTH: 29
<212> TYPE: DNA
<213> ORGANISM: Artificial Sequence
<220> FEATURE:
<223> OTHER INFORMATION: Synthesized

<400> SEQUENCE: 1
aatgatacgg cgaccaccga gatctacac            29

<210> SEQ ID NO 2
<211> LENGTH: 33
<212> TYPE: DNA
<213> ORGANISM: Artificial Sequence
<220> FEATURE:
<223> OTHER INFORMATION: Synthesized

<400> SEQUENCE: 2
acactctttc cctacacgac gctcttccga tct            33

<210> SEQ ID NO 3
<211> LENGTH: 34
<212> TYPE: DNA
<213> ORGANISM: Artificial Sequence
<220> FEATURE:
<223> OTHER INFORMATION: Synthesized

<400> SEQUENCE: 3
agatcggaag agcacacgtc tgaactccag tcac            34

<210> SEQ ID NO 4
<211> LENGTH: 24
<212> TYPE: DNA
<213> ORGANISM: Artificial Sequence
<220> FEATURE:
<223> OTHER INFORMATION: Synthesized

```
<400> SEQUENCE: 4
atctcgtatg ccgtcttctg cttg                                            24

<210> SEQ ID NO 5
<211> LENGTH: 8
<212> TYPE: DNA
<213> ORGANISM: Artificial Sequence
<220> FEATURE:
<223> OTHER INFORMATION: Synthesized

<400> SEQUENCE: 5 tatagcct                                                               8

<210> SEQ ID NO 6
<211> LENGTH: 8
<212> TYPE: DNA
<213> ORGANISM: Artificial Sequence
<220> FEATURE:
<223> OTHER INFORMATION: Synthesized

<400> SEQUENCE: 6 atagaggc                                                               8

<210> SEQ ID NO 7
<211> LENGTH: 8
<212> TYPE: DNA
<213> ORGANISM: Artificial Sequence
<220> FEATURE:
<223> OTHER INFORMATION: Synthesized

<400> SEQUENCE: 7 cctatcct                                                               8

<210> SEQ ID NO 8
<211> LENGTH: 8
<212> TYPE: DNA
<213> ORGANISM: Artificial Sequence
<220> FEATURE:
<223> OTHER INFORMATION: Synthesized

<400> SEQUENCE: 8 ggctctga                                                               8

<210> SEQ ID NO 9
<211> LENGTH: 8
<212> TYPE: DNA
<213> ORGANISM: Artificial Sequence
<220> FEATURE:
<223> OTHER INFORMATION: Synthesized

<400> SEQUENCE: 9 aggcgaag                                                               8

<210> SEQ ID NO 10
<211> LENGTH: 8
<212> TYPE: DNA
<213> ORGANISM: Artificial Sequence
<220> FEATURE:
<223> OTHER INFORMATION: Synthesized

<400> SEQUENCE: 10 taatctta                                                               8

<210> SEQ ID NO 11
```

```
<211> LENGTH: 8
<212> TYPE: DNA
<213> ORGANISM: Artificial Sequence
<220> FEATURE:
<223> OTHER INFORMATION: Synthesized

<400> SEQUENCE: 11 caggacgt                                                                     8

<210> SEQ ID NO 12
<211> LENGTH: 8
<212> TYPE: DNA
<213> ORGANISM: Artificial Sequence
<220> FEATURE:
<223> OTHER INFORMATION: Synthesized

<400> SEQUENCE: 12 gtactgac                                                                     8

<210> SEQ ID NO 13
<211> LENGTH: 8
<212> TYPE: DNA
<213> ORGANISM: Artificial Sequence
<220> FEATURE:
<223> OTHER INFORMATION: Synthesized

<400> SEQUENCE: 13 attactcg                                                                     8

<210> SEQ ID NO 14
<211> LENGTH: 8
<212> TYPE: DNA
<213> ORGANISM: Artificial Sequence
<220> FEATURE:
<223> OTHER INFORMATION: Synthesized

<400> SEQUENCE: 14 tccggaga                                                                     8

<210> SEQ ID NO 15
<211> LENGTH: 8
<212> TYPE: DNA
<213> ORGANISM: Artificial Sequence
<220> FEATURE:
<223> OTHER INFORMATION: Synthesized

<400> SEQUENCE: 15 cgctcatt                                                                     8

<210> SEQ ID NO 16
<211> LENGTH: 8
<212> TYPE: DNA
<213> ORGANISM: Artificial Sequence
<220> FEATURE:
<223> OTHER INFORMATION: Synthesized

<400> SEQUENCE: 16 gagattcc                                                                     8

<210> SEQ ID NO 17
<211> LENGTH: 8
<212> TYPE: DNA
<213> ORGANISM: Artificial Sequence
<220> FEATURE:
<223> OTHER INFORMATION: Synthesized

<400> SEQUENCE: 17
```

```
attcagaa                                                          8

<210> SEQ ID NO 18
<211> LENGTH: 8
<212> TYPE: DNA
<213> ORGANISM: Artificial Sequence
<220> FEATURE:
<223> OTHER INFORMATION: Synthesized

<400> SEQUENCE: 18 gaattcgt                                                          8

<210> SEQ ID NO 19
<211> LENGTH: 8
<212> TYPE: DNA
<213> ORGANISM: Artificial Sequence
<220> FEATURE:
<223> OTHER INFORMATION: Synthesized

<400> SEQUENCE: 19 ctgaagct                                                          8

<210> SEQ ID NO 20
<211> LENGTH: 8
<212> TYPE: DNA
<213> ORGANISM: Artificial Sequence
<220> FEATURE:
<223> OTHER INFORMATION: Synthesized

<400> SEQUENCE: 20 taatgcgc                                                          8

<210> SEQ ID NO 21
<211> LENGTH: 8
<212> TYPE: DNA
<213> ORGANISM: Artificial Sequence
<220> FEATURE:
<223> OTHER INFORMATION: Synthesized

<400> SEQUENCE: 21 cggctatg                                                          8

<210> SEQ ID NO 22
<211> LENGTH: 8
<212> TYPE: DNA
<213> ORGANISM: Artificial Sequence
<220> FEATURE:
<223> OTHER INFORMATION: Synthesized

<400> SEQUENCE: 22 tccgcgaa                                                          8

<210> SEQ ID NO 23
<211> LENGTH: 8
<212> TYPE: DNA
<213> ORGANISM: Artificial Sequence
<220> FEATURE:
<223> OTHER INFORMATION: Synthesized

<400> SEQUENCE: 23 tctcgcgc                                                          8

<210> SEQ ID NO 24
<211> LENGTH: 8
<212> TYPE: DNA
```

```
<213> ORGANISM: Artificial Sequence
<220> FEATURE:
<223> OTHER INFORMATION: Synthesized

<400> SEQUENCE: 24 agcgatag                                                                    8

<210> SEQ ID NO 25
<211> LENGTH: 33
<212> TYPE: DNA
<213> ORGANISM: Artificial Sequence
<220> FEATURE:
<221> NAME/KEY: misc_feature
<222> LOCATION: (32)..(33)
<223> OTHER INFORMATION: sulfur
<220> FEATURE:
<223> OTHER INFORMATION: Synthesized

<400> SEQUENCE: 25
acactctttc cctacacgac gctcttccga tct                                       33

<210> SEQ ID NO 26
<211> LENGTH: 31
<212> TYPE: DNA
<213> ORGANISM: Artificial Sequence
<220> FEATURE:
<221> NAME/KEY: misc_feature
<222> LOCATION: (31)..(31)
<223> OTHER INFORMATION: phosphorylation
<220> FEATURE:
<223> OTHER INFORMATION: Synthesized

<400> SEQUENCE: 26
ctgacctcaa gtctgcacac gagaaggcta g                                         31

<210> SEQ ID NO 27
<211> LENGTH: 58
<212> TYPE: DNA
<213> ORGANISM: Artificial sequence
<220> FEATURE:
<221> NAME/KEY: misc_feature
<222> LOCATION: (57)..(58)
<223> OTHER INFORMATION: sulfur
<220> FEATURE:
<223> OTHER INFORMATION: Synthesized

<400> SEQUENCE: 27
aatgatacgg cgaccaccga gatctacact ctttccctac acgacgctct tccgatct            58

<210> SEQ ID NO 28
<211> LENGTH: 24
<212> TYPE: DNA
<213> ORGANISM: Artificial Sequence
<220> FEATURE:
<223> OTHER INFORMATION: Synthesized

<400> SEQUENCE: 28
caagcagaag acggcatacg agat                                                 24

<210> SEQ ID NO 29
<211> LENGTH: 34
<212> TYPE: DNA
<213> ORGANISM: Artificial Sequence
<220> FEATURE:
<221> NAME/KEY: misc_feature
<222> LOCATION: (33)..(34)
<223> OTHER INFORMATION: sulfur
<220> FEATURE:
<223> OTHER INFORMATION: Synthesized
```

<400> SEQUENCE: 29
gtgactggag ttcagacgtg tgctcttccg atct        34

<210> SEQ ID NO 30
<211> LENGTH: 20
<212> TYPE: DNA
<213> ORGANISM: Artificial Sequence
<220> FEATURE:
<221> NAME/KEY: misc_feature
<222> LOCATION: (19)..(20)
<223> OTHER INFORMATION: sulfur
<220> FEATURE:
<223> OTHER INFORMATION: Synthesized

<400> SEQUENCE: 30
aatgatacgg cgaccaccga        20

<210> SEQ ID NO 31
<211> LENGTH: 21
<212> TYPE: DNA
<213> ORGANISM: Artificial Sequence
<220> FEATURE:
<221> NAME/KEY: misc_feature
<222> LOCATION: (20)..(21)
<223> OTHER INFORMATION: sulfur
<220> FEATURE:
<223> OTHER INFORMATION: Synthesized

<400> SEQUENCE: 31
caagcagaag acggcatacg a        21

MULTI-POSITION DOUBLE-TAG CONNECTOR SET FOR DETECTING GENE MUTATION AND PREPARATION METHOD THEREFOR AND APPLICATION THEREOF

REFERENCE TO AN ELECTRONIC SEQUENCE LISTING

The contents of the electronic sequence listing (SequenceListing3.txt; Size: 4,444 bytes; and Date of Creation: Sep. 10, 2019) is herein incorporated by reference.

TECHNICAL FIELD

The invention relates to the technical field of nucleic acid sequencing, in particular to a multi-position double-tag adapter set for detecting gene mutation, a preparation method and application thereof.

BACKGROUND TECHNOLOGY

The current second-generation sequencing is due to sample preparation (library preparation) and the instrument system itself (oxidative damage or deamination damage of DNA itself, mutations introduced by PCR enzymes during database construction, and the error is introduced when the instrument read bases during sequencing, etc.), the error probability of each base generated by sequencing is between 1/1000-1/100, that is, 1 to 10 error bases appear every 1000 bases.

In germline mutation detection, the percentage of mutation sites in samples is only 0%, 50% and 100%, so systematic base reading errors can be corrected by overlap reads of the same region in data analysis, thus achieving high sequencing accuracy.

However, there is great heterogeneity among somatic mutation sites such as tumor cell mutation. (the mutation sites in each cell may be different), and the proportion of such mutations in the sample is very low (less than 1%), such mutations cannot be distinguished using traditional bioinformatics methods (systemic base error rate as a signal-to-noise ratio between noise and tumor mutation sites is too low), so tumor site mutations cannot be accurately detected by conventional sequencing methods.

The UMI unique molecule identifier developed later can effectively solve this problem. By introducing random sequence tags into the original DNA molecule of the sample, each molecule is labeled with a unique marker. Then each molecule is amplified and sequenced in the process of building the library. Through bioinformatics analysis, most mutations (errors) in the process of building the library and sequencing can be removed, and the base of sequencing can be removed. The basic error rate is reduced to $1 \times 10^{-5}$. Assuming that the signal-to-noise ratio (SNR) of tumor mutation detection is 10 times, this method can accurately detect the mutation rate of $1 \times 10^{-4}$.

How to improve the sensitivity of mutation detection is an urgent problem to be solved.

SUMMARY OF THE INVENTION

The object of the present invention is to provide a multi-position double-tag adapter set for detecting gene mutation.

Another object of the present invention is to provide a preparation method of the multi-position double-tag adapter set.

A further object of the present invention is to provide the specific application of the above multi-position double-tag adapter set.

A multi-position and double-tag adapter set for detecting gene mutation comprises a double-tag adapter A, a double-tag adapter B and a double-tag adapter C, the double-tag adapter B and the double-tag adapter C are respectively obtained by means of synthesizing an adapter primer P5 with an adapter primer P7-A, an adapter primer P7-B and an adapter primer P7-C, all of which are modified with biotin at the 5' end, wherein:

the adapter primer P5 is obtained by SEQ ID NO:01 ligating the sequence shown in SEQ ID NO: 02 with 15 index sequence;

FFFFFEEEEEJJJJJNNNNNNNNNNNNNN, in turn connect to 5' end of SEQ ID NO:03, and SEQ ID NO:03 connect SEQ ID NO:04 through 17 index sequence, then the adapter primers P7-A is obtained;

FFFFFEEEEEKKKKKNNNNNNNNNNNNNN, in turn connect to 5' end of SEQ ID NO:03, and SEQ ID NO:03 connect SEQ ID NO:04 through 17 index sequence, then the adapter primers P7-B is obtained;

FFFFFEEEEELLLLLNNNNNNNNNNNNNN, in turn connect to 5' end of SEQ ID NO:03, and SEQ ID NO:03 connect SEQ ID NO:04 through 17 index sequence, then the adapter primers P7-C is obtained;

the FFFFF is the protective base of the restriction site, EEEEE is the restriction site, JJJJJ, KKKKK and LLLLL are the position-tag sequences, and JJJJJ, KKKKK and LLLLL are different, NNNNNNNNNNNNN is the random molecular tag sequence. FFFFF, JJJJJ, KKKKK, LLLLL and EEEEE contain but are not limited to five identical bases. The sequence of I7 index is 6-8 bases. NNNNNNNNNNNNN is 4 to 12 random bases, and there are no four consecutive identical bases.

In a preferred implementation of the present invention, the NNNNNNNNNNNNN is showed as BDHVBDHV, wherein B indicates that the position is a base other than A, D indicates that the position is a base other than C, H indicates that the position is a base other than G, V indicates that the position is a base other than T.

In a preferred implementation of the present invention, the 15 index sequence is selected from SEQ ID NO:05~12; the I7 index sequence is selected from SEQ ID NO:13~23; the sequences of JJJJJ, KKKKK and LLLLL can partially or completely overlap with the sequences of EEEEE. When the sequences are partially or completely overlapped, the base of the overlapped part appears only once.

The preparation method of the above-mentioned multi-position double-tag adapter set for detecting gene mutation includes the following steps:

(1) Annealing: after mixing the adapter primers P5, P7-A, P7-B, P7-C, buffer and proper deionized water, annealing treatment was carried out to obtain annealed adapter A, annealed adapter B and annealed adapter C.

(2) Elongating annealed adapters: elongated adapter A, B and C were obtained by polymerase elongation of annealed adapter A, B and C.

(3) First precipitation: the obtained elongated adapter A, elongated adapter B and elongated adapter C are respectively subjected to ethanol or isopropanol precipitation purification to obtain purified elongated adapter A, elongated adapter B and elongated adapter C.

(4) Enzyme digestion: restrictive endonuclease capable of producing 3'T protruding ends are added to the purified elongated adapter A, B and C respectively, for enzyme digestion, and the enzymatic digested adapter A, B and C are obtained.

(5) Second precipitation: the obtained digested adapter A, the digested adapter B and the digested adapter C are subjected to ethanol or isopropanol precipitation to obtain a double-tag adapter A, a double-tag adapter B and a double-tag adapter C.

(6) Biotin purification: the affinity purification of biotin is carried out on the double-tag adapter A, the double-tag adapter B and the double-tag adapter C obtained in step (5).

(7) Third precipitation: after precipitating and purifying the product obtained in step (6) with ethanol or isopropanol, the multi-position double-tag adapter set is obtained.

The specific application of the above multi-position double-tag adapter set is as follows:

A library construction method includes: After the 10 ng-1 μg DNA is broken into 200-500 bp DNA fragments, the terminal repair enzymes for terminal repair is added to the DNA fragments, and the A-tail was added, the above-mentioned multi-position double-tag adapter set is added for connection. After the connection is completed, 340-660 bp fragments are selected using Ampure magnetic beads or gel cutting.

A sequencing method includes the following steps:
(1) Construct the library with the above methods.
(2) Sequencing the library.

A method for determining nucleic acid sequence includes the following steps:
(1) Construct the library with the above methods.
(2) Sequencing the sequence library;
(3) The results are determined according to the sequencing results.

The method for determining the result includes the following steps:

A. Sequencing unique matching sequence with base Q value greater than 30 is selected according to the set parameters.

B. Duplication decision is made according to random tag sequence, and the base is re-corrected.

C. SNP sites are detected by SNP calling software, and the information of SNP sites is counted. The final SNP sites and corresponding MAF information are obtained.

D. the detected SNP sites and MAF information are compared with the mutant sites of the control group and the population genome variation database, the same mutant sites are filtered out, and finally left the mutant sites information is the final mutant sites information detected.

Some I5 index sequences, I7 index sequences and EEEEE sequences are listed in Tables 1 and 2. But not limited to this.

TABLE 1

Partial I5 index Sequence and I7 Index Sequence List

| I5 index sequence code | I5 index sequence | I7 index sequence code | I7 index sequence |
|---|---|---|---|
| I501 (SEQ ID NO: 05) | TATAGCCT | I701 (SEQ ID NO: 12) | ATTACTCG |
| I502 (SEQ ID NO: 06) | ATAGAGGC | I702 (SEQ ID NO: 13) | TCCGGAGA |
| I503 (SEQ ID NO: 07) | CCTATCCT | I703 (SEQ ID NO: 14) | CGCTCATT |
| I504 (SEQ ID NO: 08) | GGCTCTGA | I704 (SEQ ID NO: 15) | GAGATTCC |
| I505 (SEQ ID NO: 09) | AGGCGAAG | I705 (SEQ ID NO: 16) | ATTCAGAA |
| I506 (SEQ ID NO: 10) | TAATCTTA | I706 (SEQ ID NO: 17) | GAATTCGT |
| I507 (SEQ ID NO: 11) | CAGGACGT | I707 (SEQ ID NO: 18) | CTGAAGCT |
| I508 (SEQ ID NO: 12) | GTACTGAC | I708 (SEQ ID NO: 19) | TAATGCGC |
| | | I709 (SEQ ID NO: 20) | CGGCTATG |
| | | I710 (SEQ ID NO: 21) | TCCGCGAA |
| | | I711 (SEQ ID NO: 22) | TCTCGCGC |
| | | I712 (SEQ ID NO: 23) | AGCGATAG |

Table 2 Lists of restriction endonucleases and restriction sites available (partial)

| Restriction sites | Sequence Structure in Double-tag connectors | EEEEE Sequences in P7 Sequences of Corresponding connector Primers |
|---|---|---|
| CCTCNNNNNN N/ GGAGNNNNNN/N | T/NNNNNNGAGG /A NNNNNNCTCC | CCTCNNNNNN A/ |
| GGTGANNNNNNN N/ CCACTNNNNNNN/N | T/NNNNNNNTCACC /A NNNNNNNAGTGG | GGTGANNNNNNN A/ |
| CCTTCNNNNN N/ GGAAGNNNNN/N | T/NNNNNGAAGG /A NNNNNCTTCC | CCTTCNNNNN A/ |

-continued

| Restriction sites | Sequence Structure in Double-tag connectors | EEEEE Sequences in P7 Sequences of Corresponding connector Primers |
|---|---|---|
| GAAGANNNNNNN N/<br>CTTCTNNNNNNN/N | T/NNNNNNNTCTTC<br>/A NNNNNNNAGAAG | GAAGANNNNNNN A/ |
| GTATCCNNNNN N/<br>CATAGGNNNNN/N | T/NNNNNGGATAC<br>/A NNNNNCCTATG | GTATCCNNNNN A/ |
| ACTGGGNNNN N/<br>TGACCCNNNN/N | T/NNNNCCCAGT<br>/A NNNNGGGTCA | ACTGGGNNNN A/ |
| GACNN N/NNGTC<br>CTGNN/N NNCAG | GACNN T/NNGTC<br>CTGNN/A NNCAG | GACNN A/NNGTC |
| CCANNNN N/NNNNTGG<br>GGTNNNN/N NNNNACC | CCANNNN T/NNNNTGG<br>GGTNNNN/A NNNNACC | CCANNNN A/NNNNTGG |
| AC N/GT<br>TG/N CA | AC T/GT<br>TG/A CA | AC A/GT |
| TC N/GA<br>AG/N CT | TC T/GA<br>AG/A CT | TC A/GA |

By introducing two different UMI on the double strands of DNA and using the double strands of DNA to correct the information obtained from sequencing, the double-tag library sequencing used in the invention, it can reduce the base error rate of sequencing to $2.4 \times 10^{-6}$, so that the mutation rate of $1 \times 10^{-5}$ gene can be accurately detected and the sensitivity of gene mutation detection can be effectively improved, combined with the throughput of high-throughput sequencing, it can detect multiple mutation sites of multiple genes in a single sequence.

1. The sequencing results will be format conversion first, and the sequencing quality of the sequence will be evaluated by the positioning base at the tail of the adapter. If the positioning base can not be found, a pair of sequencing sequences will be discarded. At the same time, a pair of random base sequences at the front end of the sequence were removed and merged into the sequence ID.
2. The filtered sequence will be compared with the reference genome (Hg19, GRCh37, etc.), and the unqualified sequence (reads) (mapping quality is too low, multi-sites matching, Read1 and Read2 sequence mismatch, etc.) will be filtered according to the set parameters. Finally, a high quality unique map matching sequence (unique map reads) can be obtained for analysis.
3. Duplication is determined by using the random tag sequence added to the ID position in the first step. Sequences with the same tag and same position are considered to originate from the same initial DNA template and will be set into a cluster for base re-calibration.
4. SNP Calling software was used to detect SNP sites, and the information of SNP sites was counted. Finally, the SNP sites and related MAF information were obtained.

By comparing the detected mutation information with the control group (healthy tissue DNA from the same patient) and the population genome mutation database, the same mutation site was filtered out, and the final left mutation information was the final detected mutation site information.

The beneficial effects of the present invention are as follows:

1. The use of double Index adapters increases the number of samples for one-time sequencing (reducing the cost of sequencing). At the same time, double Index can more effectively distinguish different samples. This is very important in the detection of low-frequency mutation of genes, because the mutation rate of mutation sites detected under normal circumstances is between one thousandth and one percent. If cross-contamination occurs in different samples with different mutation sites, problems will easily arise in the determination of the final mutation sites.
2. The adapters used are long adapters, i.e. adapters with sequence timing and flow cell binding sequence (P5, P7) on the sequencer. After the adapters are linked, no further PCR amplification is needed to introduce P5 and P7 sequences, which can complete the construction of the PCR-free library and avoid the base errors (mutations) and amplified fragments introduced by the PCR in the process of Library construction. Preference and unnatural chimeric sequences produced by PCR.

The structure of the adapter of the invention is shown in FIG. 1. The Y-type structure on the left side (excluding molecular tags and position-tags) is the same as the standard adapter of the Illumina sequencing platform. Wherein, the parallel part of the Y-type adapter is complementary to the base pair, and the base of the split part has no pairing sequence; wherein the reverse complementary P5 and P7 (P7-A, P7-B and P7-C) need to be used to hybridize with the probe on the sequencing chip of Illumina sequencer, and then to amplify the signal by bridge amplification. I5 index sequence and I7 index sequence are tags of different sequencing libraries constructed to distinguish the libraries constructed by different samples. Read1 sequence and Read2 sequence are used to combine with sequencing primers for synthesizing while sequencing. Molecular tags are NNNNNNNNNNNN random tag sequence, is used to label high-throughput sequencing DNA library templates with different markers; because the sequence of molecular tags is random, it is necessary to add position bases of fixed sequence afterward to determine the position and sequence of molecular tags in data analysis.

The present invention utilizes a random tag sequence on a double-tag adapter to add a different sequence tag to each DNA template during the ligation step in the high-throughput sequencing library construction process, and then each in the subsequent PCR enrichment process, the original template is copied multiple times along with its tag sequence, resulting in multiple copies (duplications); these copies was sequenced by High-throughput sequencing, identification of the source of sequencing fragments was identified by sequence tags (used to distinguish duplication, a repetitive sequence generated in the process of Library construction, so that the sequencing results can be corrected in data analysis), and sequence correction (amplification errors and base recognition errors of sequencers) is by using template copies. After the first correction, the DNA sequence is corrected again by using the reverse complementary structure of two strands of DNA and pairing the two reverse complementary pairs of tag sequences (deamination, oxidation and other damage before and during the construction of DNA library).

3. Position tags of double-tag adapters are used to position the sequence of molecular tags, which is very important for the recognition of molecular tags. The sequence of double-tag adapters usually uses fixed sequence, such as ACT, GACT, TGACT, etc. Illumina Sequencing Platform (including Nextseq500, CN500, Miseq, Nextseq) calculates the PF value (the proportion of high quality template clusters eventually retained in the total template cluster) of the template cluster at the beginning of sequencing according to the base sequence of the first 25 cycles. Because of the limited cluster density of sequencing chips, the PF value determines output of the effective data of sequencing.

Position tags of double-tag adapters are positioned in about 9-15 cycles at the beginning of sequencing. If a single sequence is used, the low diversity of bases (the proportion of four bases) will lead to a serious decrease in PF value, which will ultimately affect the data output.

In the annealing step, the adapter primer P7-A, the adapter primer P7-B and the adapter primer P7-C respectively use three different sequence position tag sequences JJJJJ, KKKKK and LLLLL to ensure that each base in the direction of 3' to 5' is different, increasing the diversity of base in the adapter position tag, and effectively improving the PF value of the sequencing, significantly increasing the output of sequencing valid data.

4. In the process of adapter making, because the enzymatic reaction is difficult to react thoroughly, some elongated products will not be cut off during the process of enzymatic digestion. Finally, a part of the flat-end adapter with the protective base of the enzyme restriction site (about 8 bp) will remain. Each of the 3'end of the P5 sequence and 5'end of the P7 sequence of the flat-end adapter has one OH group each. During the joining process of the adapter (FIG. 2), this part of the flat-end adapters are connected by the 3'end OH group of the P5 sequence and the 5'end phosphoric acid set of the DNA double-stranded template (the other chain can't be connected because both are OH groups). (1) If flat-end adapters are added to both ends of the double-stranded DNA template, the subsequent PCR amplification can not be carried out because there is a gap in the adapter junctions at both ends of the template, resulting in the loss of some DNA templates. (2) If one end of DNA template is connected with a flat-end adapter and the other end is connected with a normal adapter, then the P5 sequence of flat-end adapter-DNA template single-strand-normal adapter P7 sequence template will be amplified as an effective PCR template, and the other strand of DNA template will be lost because of the gap between the two sides of the adapter. (1) and (2) will cause the loss of DNA template. In addition, in the case of (2), the loss of one strand in DNA double-strand will lead to the loss of complementary strands in template DNA during double-stranded random tag correction, which will affect the performance of double-strand correction. The residue of 3'terminal protective base in P5 chain of flat-end adapter contaminates template sequence, resulting in waste of partial data and loss of sequencing information in Read1 sequence of sequencing results.

The invention introduces biotin modification at the 5end of P7 adapter primers. After annealing and elongation, P5 and P7 adapter primers all carry biotin markers at the 5' end of P7 chain. After enzymatic digestion, the normal biotin makers of the adapters was lost, while the flat-end adapters (i.e., the residual elongation products) which were not digested by enzymatic digestion still had biotin makers. After purification by avidin magnetic beads, the residual flat-end adapters could be removed, and the residual protective base sequence of the adapters caused by incomplete enzymatic digestion could be effectively removed. The schematic diagram is shown in FIG. 1.

DRAWINGS

DETAILED DESCRIPTION

The following is a further description and description of the technical scheme of the present invention through specific embodiments in conjunction with the accompanying drawings.

Embodiment 1: Preparation of Single Position Double-Tag Adapter

Two primers, adapter primer P5 and adapter primer P7 (the adapter primer P5 was obtained by SEQ ID NO:01 ligating the sequence of SEQ ID NO: 02 with 15 index sequence, the adapter primer P7 was obtained by SEQ ID NO:03 ligating the sequence of SEQ ID NO: 04 with 17 index sequence, wherein, FFFF-FEEEEEJJJJJNNNNNNNNNNNNN, in turn connecting to 5' end of SEQ ID NO:03; synthetic manufacturers: Bioengineering (Shanghai) Co., Ltd.) were diluted with ddH$_2$O (or TE buffer) to 100 µM.

Wherein FFFFF is the protective base of restriction site, EEEEE is the restriction site, DDDDD is the position tag sequence, NNNNNNNNNNNN is random molecule maker, the 15 index sequence is selected from SEQ ID NO:5-12. The 17 index sequence is selected from SEQ ID NO:13-24.

Meanwhile, FFFFF/DDDDD/EEEEE/includes but is not limited to five identical bases. NNNNNNNNNNNNNNNN is 4 to 12 random bases, and there are no four consecutive identical bases.

Figure 3:
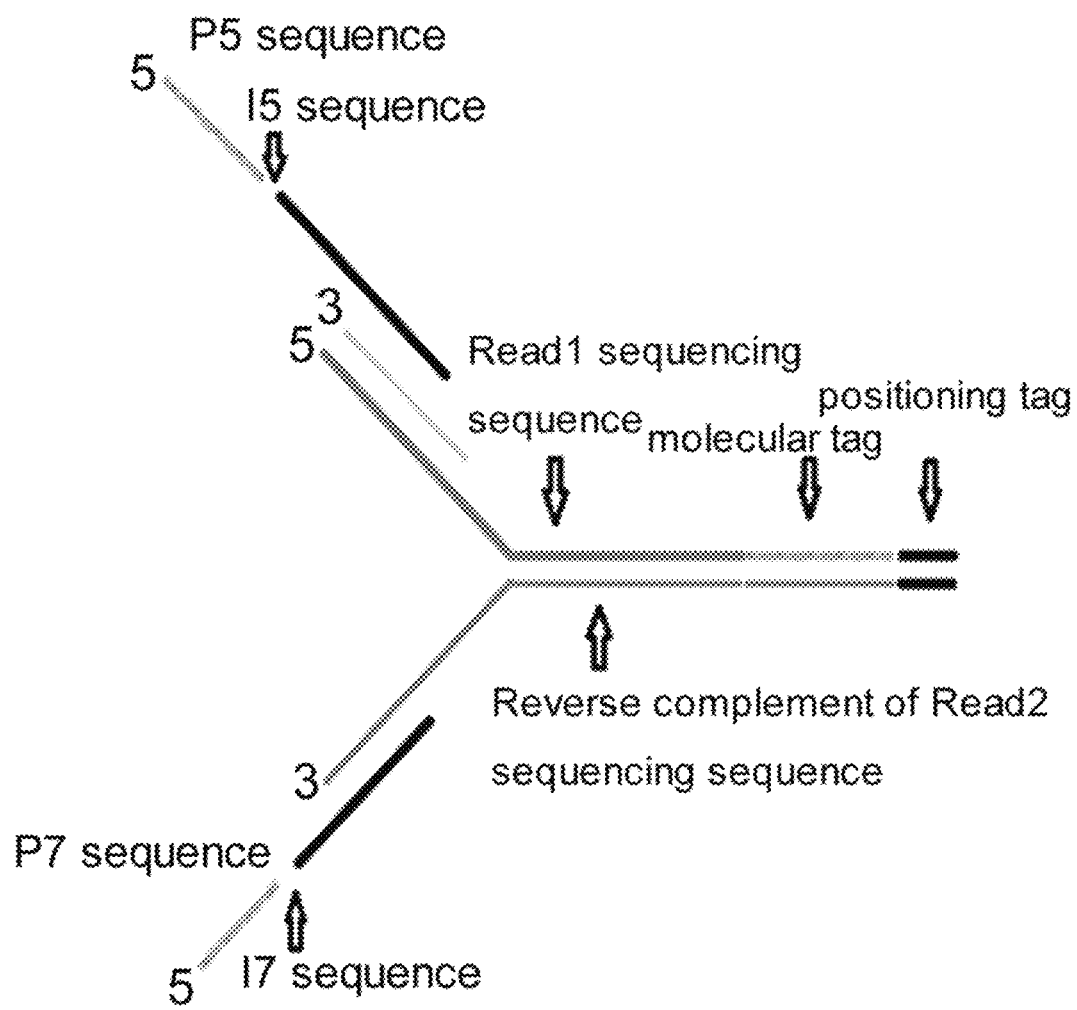
FIG. 3 is a schematic diagram of a double-tag adapter of introducing Index by PCR in the present invention.

The preparation method of the single position double-tag adapter is as follows (as shown in FIG. 3):

(1) Annealing: The following system was prepared in 0.2 mL EP pipe: adapter primer P5:10 µL, adapter primer P7: 10 µL, NEB buffer2: 3 µL, ddH2O: 7 µL; in total 30 µL. The system was annealed on a polymerase chain reaction (PCR) instrument: 95° C., 5 min; gradient cooling of 95° C.~24° C., 0.2-0.5° C./s; maintenance at 24° C.;

(2) Amplified annealed fragments: In the original PCR tube, add: 10×NEB buffer: 2 µL, 10 mM dNTP mix: 5 µL, ddH2O: 8 µL, Klenow exo-(5U/µL): 5 µL, 50 µL in total. After mixing, it was placed at 37° C. for 1 hour.

(3) First precipitation: ⅒ volume of NaAC (3M) and 2.5 times volume of absolute ethanol were added to the product of the step (2), and then mixed and placed at −20° C. for 2 h; centrifuged at 13000 g for 30 min; the supernatant was removed, 600 mu L 70% ethanol was added for rinsing and precipitating, centrifuged at 13000 g and 4° C. for 30 min; after the supernatant was removed, the DNA was dried at room temperature for 5-10 minutes, and the DNA was re-suspended with 30 µL ddH$_2$O.

(4) Enzymatic hydrolysis (for example, HpyCH4III endonuclease, restriction site: ACNGT, the corresponding primer P7 sequence EEEEE is ACAGT): The product obtained by step (3) was 30 µL and 5 µL 10×NEB CutSmart buffer was added:ddH$_2$O: 10 µL, HpyCH4III(5 U/µL): 5 µL, 50 µL in total. After mixing, enzymatic hydrolysis was carried out at 37° C. for 16 hours.

Figure 1:
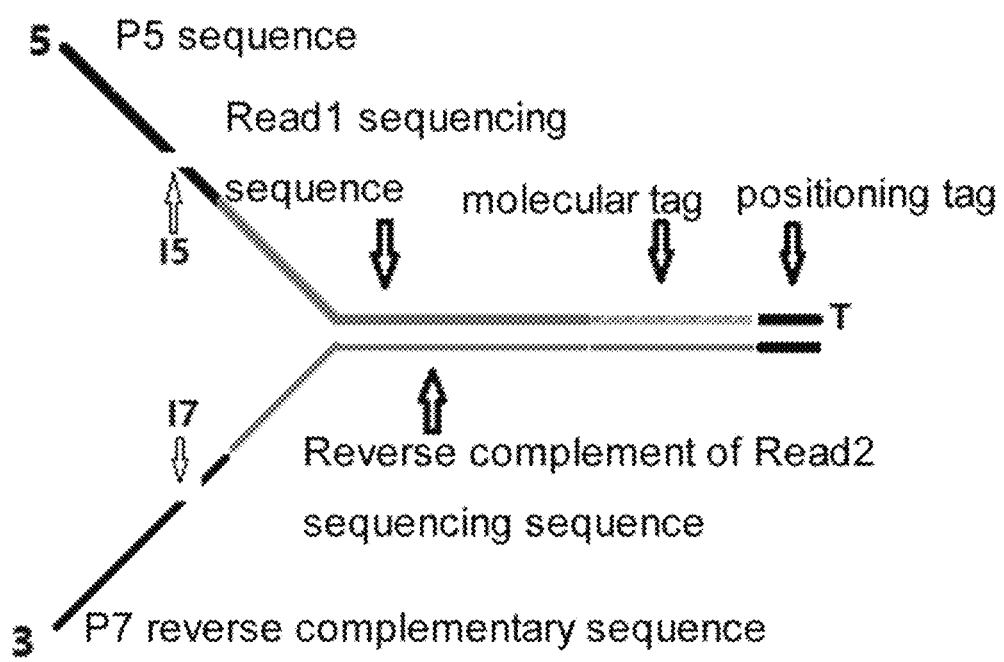
FIG. 1 is a schematic diagram of a single position double-tag adapter prepared by embodiment 1 of the present invention.
Figure 2:
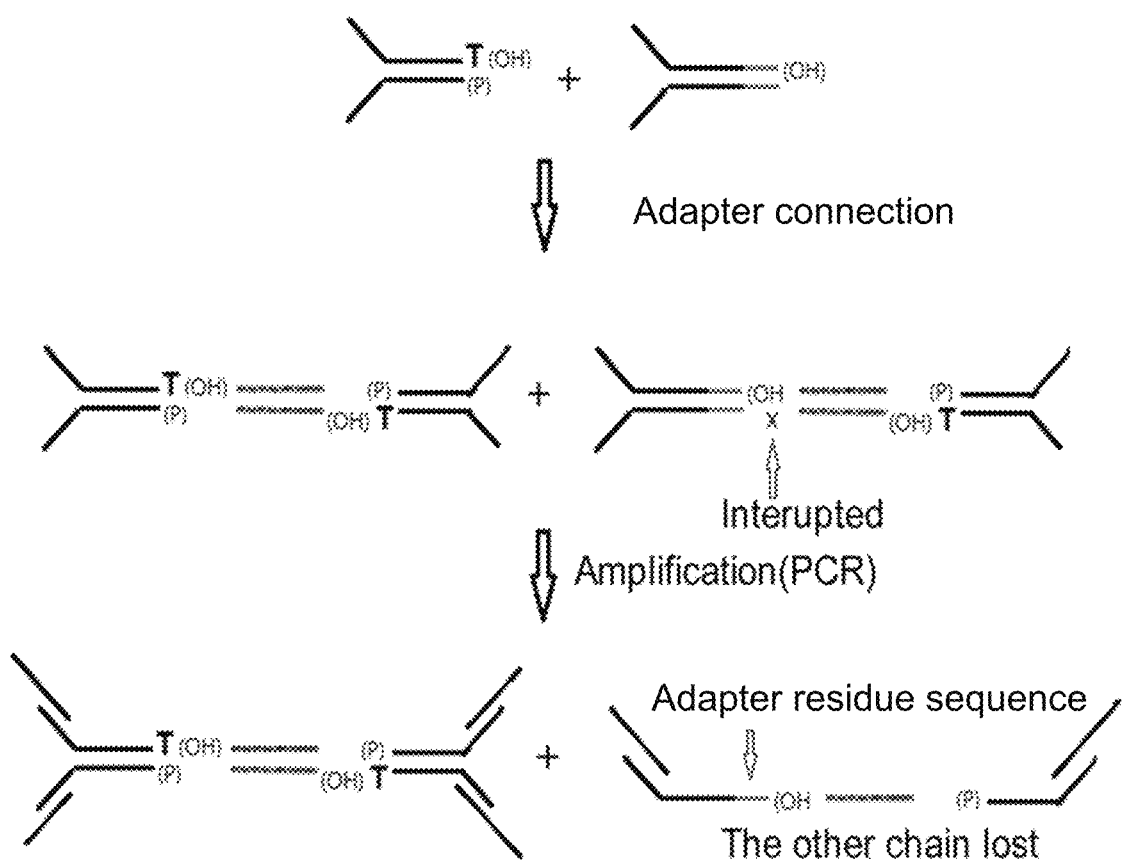
FIG. 2 is a schematic diagram of the effect of flat-end adapter (residual elongated adapter) on sequencing libraries in the present invention.

(5) Second precipitation:⅒ volume of NaAC (3M) and 2.5 times volume of absolute ethanol were added to the product of the step (4), and then mixed and placed at −20° C. for 2 hours; centrifuged for 30 min at 14 000 g and 4° C.; the supernatant was removed, 600 µL 70% ethanol was added for rinsing and precipitating, centrifuged at 13000 g and 4° C. for 30 min; The supernatant was removed, the DNA was dried at room temperature for 5-10 minutes, and the DNA was re-suspended with 26 µL TE low buffer. The final single position double-tag adapter (25 µM, the structure as shown in FIG. 2) was obtained and sub-packed at 5 µL and frozen at −80° C. for reserve.

Embodiment 2: Detection of Plasma DNA Mutation Rate by Single Position Double-Tag Adapter In this embodiment: The protective base of the single position double-tag adapter prepared by embodiment 1 is TCTTCT. The sequence of restriction sites was AC|AGT| (position base in box, partial overlap of restriction site and position base). The molecular tag is BDHVBDHV.

The combination of I5 index sequence and I7 index sequence may be:I501-I701, I502-I702, I503-I703, I504-I704, I505-I705, I506-I706, I507-I707, I508-I708, I501-I707, I502-I708, I503-I709, I504-I710. (The base sequence corresponding to the serial number is shown in Table 1)

Sample selection and quality control: Five plasma samples from patients with lung cancer were collected, and plasma DNA was extracted by QIAGEN plasma DNA extraction kit. The purity of DNA samples was determined by spectrophotometer (A260/280 was required to be between 1.8 and 20). Then the DNA concentration was determined by Qubit 2.0 (the total amount was between 5-15 ng), the DNA fragment distribution was detected by D1000 chip (Agilent) and the mutation rate of EGFR gene T790M sites (1.9%, 0.8%, 0.18%, 0.12% and 1.44%) was determined by digital PCR (Bio-rad).

Library Construction: The KAPA DNA library kit was used to construct the library, and all DNA samples were used to construct the library.

KAPA HTP Library Preparation Kit Illumina® Platforms, end-repair enzymes and end-repair buffers used in the following experiments were all derived from the kit.

Figure 4:
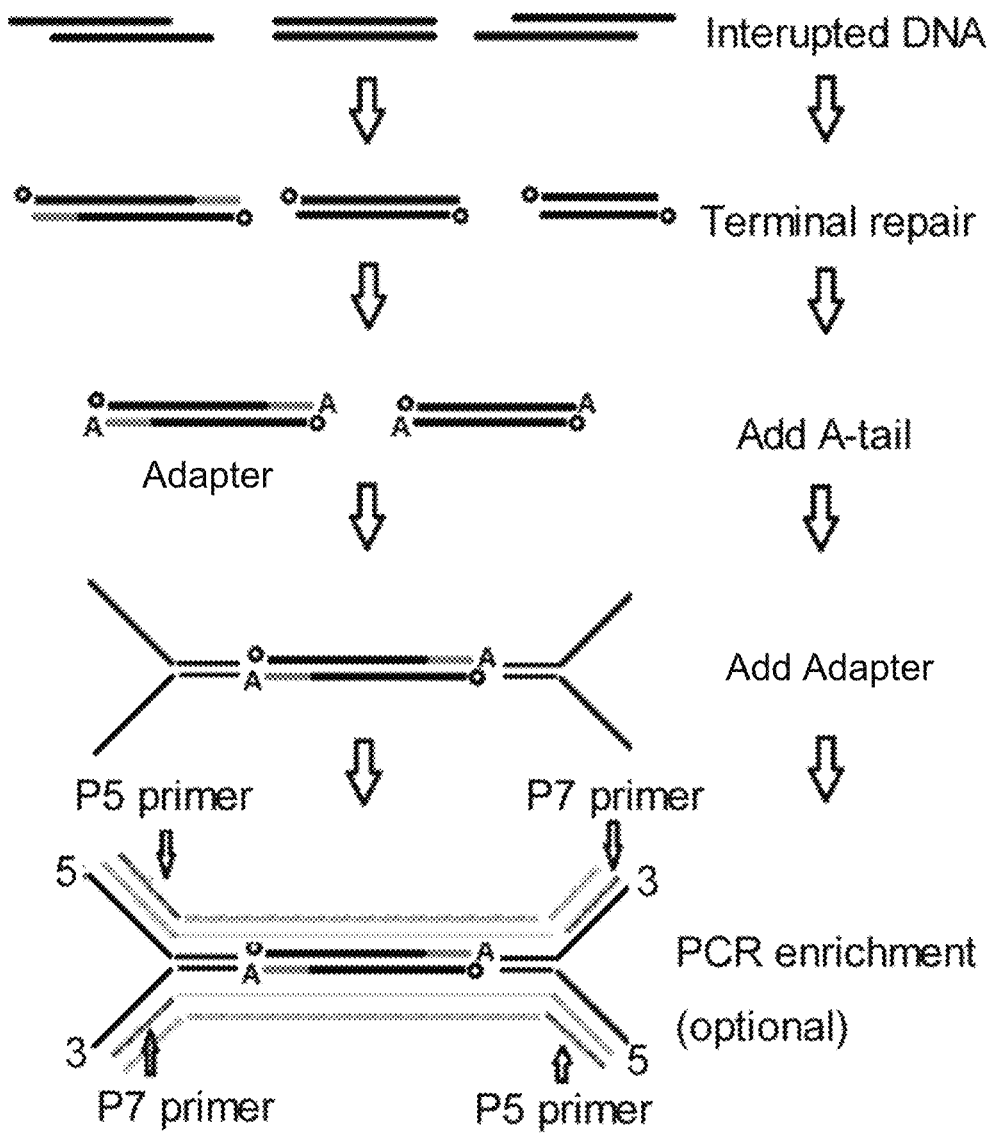
FIG. 4 is a flow chart for the construction of a single position and double-tag adapter Library in embodiment 2 of the present invention.

End repair of DNA samples (adding 7 µL 10× end repair buffer, 5 µL end repair enzyme, 20° C., 30 min); after purification, the product was added A-tail with A-taling enzyme (5 µL 10× end repair buffer, 3 µL end repair enzyme 30° C., 30 min), the product was divided into two parts after purification, and the single position double-tag adapter prepared in Embodiment 2 was used in the connecting step (a single position double tag adapter was added to the fragment with the A tail according to a 10:1 molar ratio) to build the library (As shown in FIG. 4) or ordinary building adapter (the sequence was as SEQ ID NO: 24 and 25), 10 µL of 5× ligation buffer+5 µL of T4 DNA ligase was added and connect at 20° C. for 20 min, the product was purified by two steps of 1× Ampure magnetic beads, and the purified product was amplified by KAPA high fidelity enzyme mix (25 µL) and upstream and downstream amplification primers (25 µM) with 1 µL each.

Wherein the common library building adapter was added as a control. In the experimental set, the single position double-tag adapter which was prepared in embodiment 2 was added. The steps of the control group were the same as those of the experimental set, but the sequence of adapters used were different.

The upstream and downstream amplification primers used in the common Library building adapter sample set were general primers (SEQ ID NO:5) and index primers (SEQ ID NO:6). The upstream and downstream primers used in the single position and double-tag adapter sample set prepared by embodiment 2 were PCR-P5 primers+PCR-P7 primers.

Common Library building adapter sequence information:

```
                                      SEQ ID NO: 24
5'-ACACTCTTTCCCTACACGACGCTCTTCCGATC-s-T-3'

SEQ ID NO: 25
3'-CTGACCCTCAAGTCTGCACACGAGAAGGCTAG-p-5'
```

The sequence of upstream and downstream primers corresponding to common Library building adapters:

```
Universal primers:
                                      SEQ ID NO: 26
5'-AATGATACGGCGACCACCGAGATCTACACTCTTTCCCTACACGACGCT
CTTCCGATC-s-T-3'
(-s-denotes thio, the same as the following)

Index primers:
obtained by SEQ ID NO: 27 connecting SEQ ID NO: 28
through I7 index sequence:
                                      SEQ ID NO: 27
5'-CAAGCAGAAGACGGCATACGAGAT SEQ ID NO: 28
GTGACTGGAGTTCAGACGTGTGCTCTTCCGATC-s-T-3'
```

Wherein I7 Index sequence is selected from SEQ ID NO:13-24.

The sequence of P5 and P7 primers corresponding to the single position double-tag junction prepared by embodiment 1: When the adapters were added to the single position double-tag adapters prepared by embodiment 1, the following primer sequences were used:

```
PCR-P5:
                                    SEQ ID NO: 29
AATGATACGGCGACCACCG-s-A

PCR-P7:
                                    SEQ ID NO: 30
CAAGCAGAAGACGGCATACG-s-A
```

Capture: According to Roche SeqCap EZ custom kit (250k) the library target capture is carried out, the capture library was qualified and subjected to sequencing (Agilent 2100/2200 judges the size distribution of the library fragment, for example, the size of the insert (template) is 200-350 bp when the library is constructed, after two end adapters P5,P7 were added, it increase 140 bp, the size of the library should be 340 bp-490 bp; QPCR was used to judge the capture effect—if the average enrichment factor is less than 10, the capture failed and needed to be recaptured).

Result: The sequencing depth of each sample was 20000× and the raw data of the sample of sequence was 8.20 G, clean data Q20 was 94.25%, Q30 was 0.3%, mapping rate was 99.9% and coverage was 99.89%. In terms of detection results, two of 1.9% and 1.44% of the sample mutation sites can be accurately detected in the common adapter sample set, while all sample mutation sites of 1.9%, 0.8%, 0.18%, 0.12% and 1.44% can be detected in the single position and double-tag adapter sample (based on the mutation sites and mutation rate information detected by digital PCR before the establishment of the database, high-throughput sequencing data were analyzed by software (FastQC, samtools, BWA/bowtie2, GATK, Freebayes/picard, etc.), to analyze whether these sites have mutations and mutation rates, compare them with the results of digital PCR, and determine the detection rate). The detection rate was 100% (compared with the results of digital PCR, if digital PCR detects 10 low-frequency mutation sites in these 5 samples, if high-throughput sequencing can detect all 10 sites, the detection rate is 100%, if five sites were detected, the detection rate would be 50%).

Embodiment 3: Detection of Mutation Rate of Single Position Double-Tag Adapter Cell Lines NCI-H1650 and HCT cell lines were selected as experimental materials. NCI-H1650 cell DNA was incorporated into HCT cell DNA in 10%, 1% and 0.1% mass ratio, respectively. In addition, 100% DNA of NCI-H1650 and HCT cell were used as two samples, respectively, corresponding to 10%, 1%, 0.1%, NCI-H1650 and HCT sets. (NCI-H1650 and HCT sets are only used to determine the genetic background of DNA used for mixing proportions, i.e. allele sites information, such as heterozygosity and homozygosity. Through the sequencing information of these two samples, some homozygous base sites can be found, and then the sites with different bases at the same site can be selected as statistical analysis sites for other sample sets.)

Figure 5:
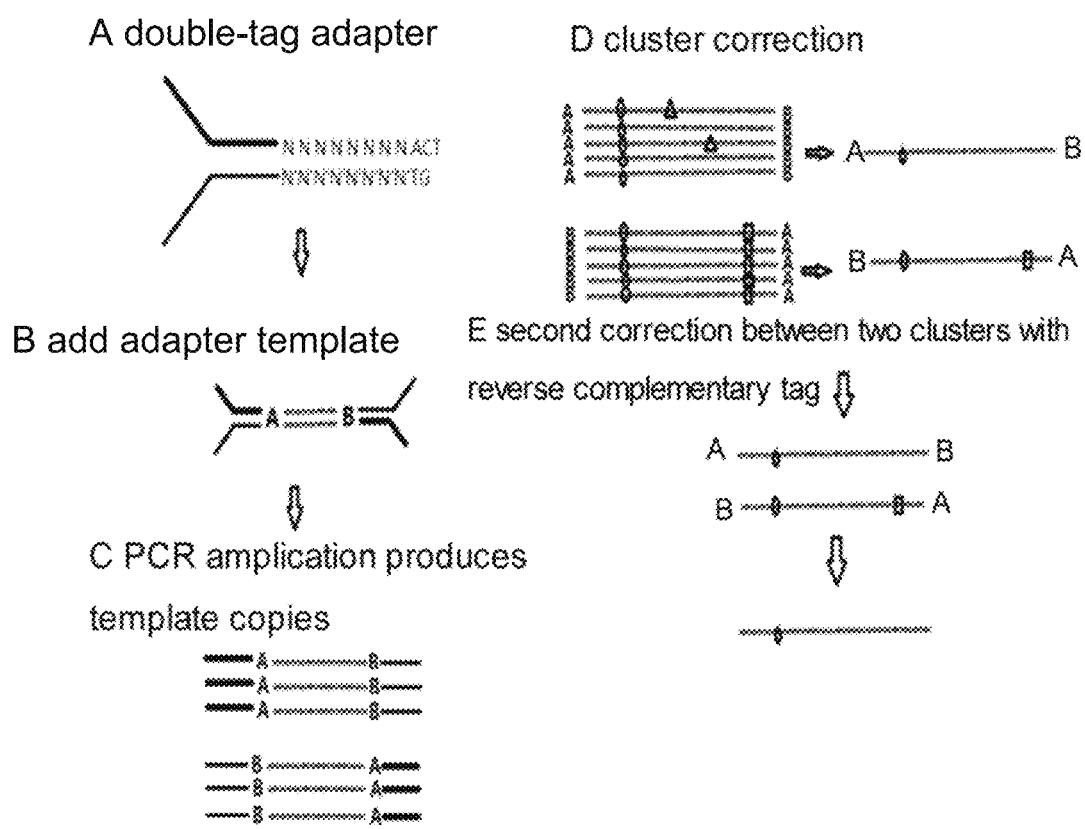
FIG. 5 is a flow chart for identifying cell mutations by single position double-tag adapter in embodiment 3 of the present invention.

DNA samples were fully blended and then taken 2 μg for DNA library preparation (KAPA DNA library kit). Wherein 10%, 1% and 0.1% samples were equally divided into two sets after adding A-tail step, adding common adapters (such as SEQ ID NO:3 and SEQ ID NO:4) and single position double-tag adapter (as shown in FIG. 5) prepared in embodiment 1, and then subsequent library preparation and capture steps were carried out. Roche SeqCap EZ custom kit (250k) is used in capture step, and finally sequenced on the computer. The depth of the sequence is 2000×. The sequencing results are detected by filtered Q30 unique mapping reads. the single position double-tag adapter FFFFF is TCTTCT and EEEEE is ACAGT;DDDDD is AGT; it overlaps with the EEEEE sequence mentioned above.

The NNNNNNNNNNNN is showed as BDHVBDHV, wherein B indicates that the position is a base other than A, D indicates that the position is a base other than C, H indicates that the position is a base other than G, V indicates that the position is a base other than T.

Result: Firstly, the data of NCI-H1650 and HCT samples were analyzed, and the base MAF (secondary allele frequency) in the 250 Kbp capture region of Roche capture chip was found according to the SNP detection information. The base sites with 0% of MAF (SNP homozygous negative) and 100% of base sites (SNP homozygous positive) were screened out (the actual criterion is to set a threshold, such as 0.1%. If the MAF value of a site is less than 0.1%, it is considered that the sites is 0% base site, that is, SNP homozygous negative sites; 100% sites is analogous in turn). Screening the corresponding sites in two cell lines (the same position in the genome), one sites was homozygous positive and the other was homozygous negative. These sites were used as the statistical detection rate and false-positive and false-negative information of the analysis site samples of other sample sets.

In NCI-H1650 and HCT sets (100%) 178 homozygous allele SNP sites were detected (i.e., each site was homozygous negative in one cell line and homozygous positive in another cell line). Then, 10%, 1% and 0.1% samples of different adapters were analyzed for these 178 sites, and the mutation rate of 178 sites in different proportion samples (heterozygosity) were 10%, 1% and 0.1% respectively. The positive detection rate of common adapter was 100% in 10% sample set, 98.86% in 1% sample set and 81.29% in 0.1% sample set. The detection rates of single position and double-tag adapters prepared by embodiment 1 were 100% in 10%, 1% and 0.1% sets. False positive rate: under 1% sensitivity, the false positive rate of common adapters was 0.01%, and under 0.1% sensitivity, the false positive rate of common adapters was more than 5%. The false positive rate of single position double-tag adapter prepared by embodiment 1 was 0.001% at the sensitivity of 0.1%. (The site whose sensitivity value exceeded a certain threshold was considered to be the detected mutation site. For example, 1% sensitivity was defined as the mutation site whose threshold value of base mutation frequency was 1%, and the site whose sensitivity value exceeded 1% was considered to be the detected mutation site.)

Embodiment 4: Preparation of Multi-Position Double-Tag Adapter Set adapter primers P7-A, P7-B and P7-C (synthesizer: Biotechnology and Bioengineering (Shanghai) Co., Ltd.) were diluted with ddH$_2$O to 100 μM, respectively.

The adapter primer P5 is obtained by SEQ ID NO:01 ligating the sequence shown in SEQ ID NO: 02 with I5 index sequence;

FFFFFEEEEEJJJJNNNNNNNNNNNNN, in turn connect to 5' end of SEQ ID NO:03, and SEQ ID NO:03 connect SEQ ID NO:04 through I7 index sequence, then the adapter primers P7-A is obtained;

FFFFFEEEEEKKKKKNNNNNNNNNNNN, in turn connect to 5' end of SEQ ID NO:03, and SEQ ID NO:03 connect SEQ ID NO:04 through I7 index sequence, then the adapter primers P7-B is obtained;

FFFFFEEEEELLLLLNNNNNNNNNNNN, in turn connect to 5' end of SEQ ID NO:03, and SEQ ID NO:03 connect SEQ ID NO:04 through I7 index sequence, then the adapter primers P7-C is obtained;

the FFFFF is the protective base of the restriction site, EEEEE is the restriction site, JJJJJ, KKKKK and LLLLL are the position-tag sequences, and JJJJJ, KKKKK and LLLLL are different, NNNNNNNNNNNN is the random molecular tag sequence. FFFFF, JJJJJ, KKKKK, LLLLL and EEEEE contain but are not limited to five identical bases. The sequence of I7 index is 6-8 bases. NNNNNNNNNNNN is 4 to 12 random bases, and there are no four consecutive identical bases.

Preferably, the NNNNNNNNNNNN is showed as BDHVBDHV, wherein B indicates that the position is a base other than A, D indicates that the position is a base other than C, H indicates that the position is a base other than G, V indicates that the position is a base other than T. The 15 index sequence is selected from SEQ ID NO:05~12; The I7 index sequence is selected from SEQ ID NO:13~23.

Preferably, the sequences of JJJJJ, KKKKK and LLLLL can overlap partially or completely with the sequences of EEEEE. When the sequences are partially or completely overlapped, the base of the overlapped part appears only once.

Figure 6:
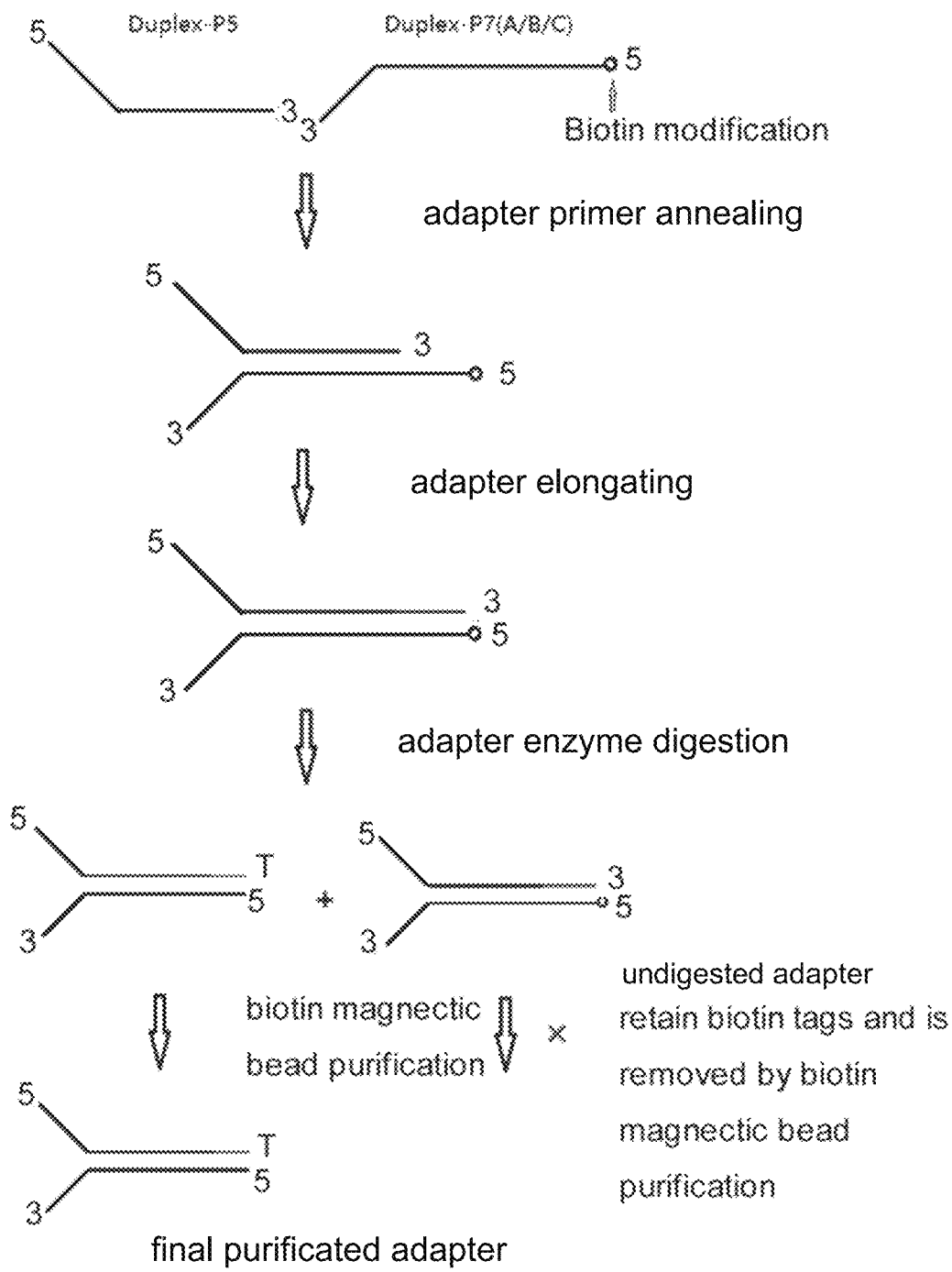
FIG. 6 is a schematic diagram of the preparation process of the multi-position double-tag adapter set in embodiment 4 of the present invention.

The preparation process of the multi-position double-tag adapter set is as follows (FIG. 6):

(1) Annealing: after mixing the adapter primers P5, P7-A, P7-B, P7-C, buffer and proper deionized water, annealing treatment was carried out to obtain annealed adapter A, annealed adapter B and annealed adapter C; specifically: the following systems are prepared in a 15 mL centrifugal tube: adapter primer P5:1 mL, P7-A:334 µL, P7-B:334 µL, P7-C: 334 µL, NEB buffer2: 300 µL, ddH$_2$O: 700 µL; 3 mL in total. After mixing the system, the following reactions were carried out: In the water bath pot at 95° C. for 5 minutes. Then immediately it is putted into a beaker filled with hot water at 95° C., slowly cooling to 24-27° C. at room temperature.

(2) Elongating annealed adapters: the obtained annealed adapter A, annealed adapter B and annealed adapter C were elongated by polymerase chain reaction to obtain elongated adapter A, elongated adapter B and elongated adapter C. In the original 15 mL centrifugal tube, add: 10×NEB buffer: 200 µL, 25 mM dNTP mix: 200 µL, 500 mM DTT: 6 µL, Klenow exo-(5 U/µL): 100 µL, supplemented with ddH$_2$O to 5 mL. After blending, the mixture was rotated in a 37° C. thermostat and incubated for 1 hour.

(3) First precipitation: the purified elongated adapter A, B and C were obtained by precipitation and purification with ethanol or isopropanol, respectively, specifically ¹⁄₁₀ volume of NaAC (3M) and 2.5 times volume of absolute ethanol were added to the product of the step (2), and then mixed and placed at −20° C. for 2 h; centrifuged at 13000 g for 30 min; the supernatant is removed, 5 ml 70 volume % ethanol was added to rinse and precipitate, centrifuged at 13000 g and 4° C. for 30 min; The supernatant was removed, the DNA was dried at room temperature for 20-30 minutes, the DNA was suspended with 3 mL ddH$_2$O, and the concentration was measured by Quantus.

(4) Enzyme digestion: the purified elongated adapter A, B and C were added to restrictive endonuclease capable of producing 3'T protruding ends, respectively, for enzyme digestion, and the enzymatic digested adapter A, B and C were obtained; specifically (Take HpyCH4III endonuclease as an example, the restriction site: ACNGT, corresponding primer P7 sequence EEEEEE was changed to ACAGT):the product obtained from the above step (3) is added 10×NEB CutSmart buffer according to its mass x(µg): 2×µL, HpyCH4III(5 U/µL): 2×µL, supplemented with ddH$_2$O to 20×µL, mixed, incubated in a 37° C. incubator, enzymatic hydrolysis for 16 h;

(5) Second precipitation: the obtained digested adapter A, the digested adapter B and the digested adapter C are subjected to ethanol or isopropanol precipitation to obtain a double-tag adapter A, a double-tag adapter B and a double-tag adapter C; specifically: ¹⁄₁₀ volume of NaAC and 2.5 times volume of absolute ethanol were added to the product of the step (4), and then mixed and placed at −20° C. for 2 hours; centrifuged for 30 min at 14 000 g and 4° C.; the supernatant was removed, 10 m L 70% ethanol was added or rinsing and precipitating, centrifuged at 13000 g and 4° C. for 30 min; the supernatant was removed, the DNA were dried at room temperature for 20-30 minutes and suspended with 2 mL ddH$_2$O.

(6) Biotin purification: the affinity purification of biotin was carried out on the double-tag adapter A, the double-tag adapter B and the double-tag adapter C obtained in step (5); specifically:2 mL Dynabeads MyOne Streptavidin C1 magnetic beads were rinsed with 1×B&W buffer magnetic beads and then re-suspended with 2 mL 2×B&W buffer magnetic beads. 2 mL the products obtained from step (5) were added to the magnetic beads, incubated at 4° C. for 30 minutes, and placed on the magnetic rack, and the supernatant was taken to a new 50 mL centrifugal tube.

(7) Third precipitation: after precipitating and purifying the product obtained in step (6) with ethanol or isopropanol, the multi-position double-tag adapter set is obtained, specifically: ¹⁄₁₀ volume of NaAC and 2.5 times volume of absolute ethanol were added to the product of the step (6), and then mixed and placed at −20° C. for 2 hours; centrifuged for 30 min at 14 000 g and 4° C.; the supernatant was removed, 10 m L 70% ethanol was added or rinsing and precipitating, centrifuged at 13000 g and 4° C. for 30 min; the supernatant is removed, the DNA is dried at room temperature for 20-30 minutes and re-suspended with 1.5 mL TE low buffer, that is, the multi-position double-tag adapter set, which is subpacked after qualified, is frozen at −20° C. for reserve.

Embodiment 5: Improvement of Sequencing PF Value of the Multi-Position Double-Tag Adapter Set A library was constructed after 30 ng interrupted Leukocyte DNA (average length 220 bp). The experiment was divided into two sets. One set constructed the library with single position double-tag adapter prepared by embodiment 1 and the other set constructed the library with multi-position double-tag adapter set prepared by embodiment 4. The library kit uses NEBNext Ultra II DNA Library Prep Kit. The library construction steps are as follows:

(1) 30 ng interrupted DNA was added into 7 µL NEBNext ULtra II End Prep Reaction Buffer and 3 µL NEBNext ULtra II End Prep Enzyme Mix, and the volume was supplemented with deionized water to 60 µL. The DNA was at 20° C., 30 min→65° C., 30 min→4° C. maintained on the PCR.

(2) In the system, 1 µL adapter (the single position double-tag adapter or the multiple-position double-tag adapter set) was added, then a 30 µL NEBNext ULtra II Ligation Master Mix and 1 µL NEBNext Ligation Enhancer were added, and the reaction time was 15 minutes after mixing at 20° C. The conjugated product was purified by 0.9× Ampure magnetic beads and eluted by 23 μL purified water.

(3) 23 μL of the above conjugated product, 1 μL (25 μM) of each of the I5 and I7 index primers, NEBNext ULtra III Q5 Master Mix respectively were added to the PCR tube. After mixing, the following reactions were performed on the PCR apparatus:

98° C., 30s;
98° C., 10s→65° C., 75s (8 cycles);
65° C., 5 min;
Maintenance at 4° C.

After the completion of the PCR, the purified product was purified with 0.9× magnetic beads, and then the quality control was carried out with Qubit 2.0 (or Quantus) and Agilent 2100 Bioanalyzer (or Agilent 2200 TapeStation).

After the quality control of the library is qualified, the NextSeq500 platform is used for sequencing. The sequencing reagent is Mid Output Kit (300 cycles). Phix incorporation ratio is 1%. Each library is sequenced separately on the computer. The experiment was repeated three times and sequenced on computer respectively. The sequencing platform was NextSeq500, the sequencing reagent was Mid Output kit (300 cycles), and Phix incorporation rate was 1%. The quality control of the sequencing results was as follows:

| Experience set | Cluster density | Phix ratio (%) | PF value | Q30 |
|---|---|---|---|---|
| Single Position Double-tag connector Library-1 | 190 K/mm² | 1.2% | 33.80% | 90.4% |
| Single Position Double-tag connector Library-2 | 186 K/mm² | 0.8% | 31.50% | 85.8% |
| Single Position Double-tag connector Library-3 | 200 K/mm² | 1.5% | 33.20% | 82.0% |
| Multi-Position and Double-tag connector set Library-1 | 200 K/mm² | 0.9% | 87% | 88.6% |
| Multi-Position and Double-tag connector set Library-2 | 181 K/mm² | 1.2% | 90% | 87.3% |
| Multi-Position and Double-tag connector set Library-3 | 210 K/mm² | 1.3% | 91% | 90.1% |

Embodiment 6: After Purification of Biotin, Residue of the Sequence of Adapter Library Building The library was constructed with 30 ng interrupted Leukocyte DNA (average length 220 bp), the experiment was divided into two sets: one set constructed the library with single position double-tag adapter prepared by embodiment 1, the other set constructed the library with multi-position double-tag adapter set prepared by embodiment 4, and the library kit was NEBNext ULtra II DNA Library Prep Kit. The steps of library construction are as follows:

(1) 30 ng interrupted DNA was added into 7 μL NEBNext ULtra II End Prep Reaction Buffer and 3 μL NEBNext ULtra II End Prep Enzyme Mix, and the volume was supplemented with deionized water to 60 μL. The DNA was at 20° C., 30 min→65° C., 30 min→4° C. maintained on the PCR.

(2) In the system, 1 μL adapter (the single position double-tag adapter or the multiple-position double-tag adapter set) was added, then a 30 μL NEBNext ULtra II Ligation Master Mix and 1 μL NEBNext Ligation Enhancer were added, and the reaction time was 15 minutes after mixing at 20° C. The conjugated product was purified by 0.9× Ampure magnetic beads and eluted by 23 μL purified water.

(3) 23 μL of the above conjugated product, 1 μL (25 μM) of each of the I5 and I7 index primers, NEBNext ULtra III Q5 Master Mix respectively were added to the PCR tube. After mixing, the following reactions were performed on the PCR apparatus:

98° C., 30s;
98° C., 10s→65° C., 75s (8 cycles);
65° C., 5 min;
Maintenance at 4° C.

After the completion of the PCR, the purified product was purified with 0.9× magnetic beads, and then the quality control was carried out with Qubit 2.0 (or Quantus) and Agilent 2100 Bioanalyzer (or Agilent 2200 TapeStation).

After the quality control of the library is qualified, the NextSeq500 platform is used for sequencing. The sequencing reagent is Mid Output Kit (300 cycles). Phix incorporation ratio is 1%. The amount of data in each library was 1 GB. The sequencing results were as follows:

| Experience set | Data amount | Q30 | unMapped % | Read1 connector residue | Read2 connector residue |
|---|---|---|---|---|---|
| Single Position Double-tag connector Library-1 | 955.13M | 85.03% | 1.50% | 4.66% | 0.15% |
| Single Position Double-tag connector Library-2 | 1.09 G | 84.86% | 1.39% | 4.64% | 0.11% |
| Single Position Double-tag connector Library-3 | 1.13 G | 84.89% | 1.44% | 4.12% | 0.16% |
| Multi-Position and Double-tag connector set Library-1 | 956.17M | 84.68% | 0.99% | 0.07% | 0.07% |
| Multi-Position and Double-tag connector set Library-2 | 1.14 G | 84.82% | 0.57% | 0.08% | 0.06% |

-continued

| Experience set | Data amount | Q30 | unMapped % | Read1 connector residue | Read2 connector residue |
|---|---|---|---|---|---|
| Multi-Position and Double-tag connector set Library-3 | 1.08 G | 85.50% | 0.51% | 0.11% | 0.07% |

As mentioned above, it is only a better embodiment of the present invention, so the scope of implementation of the present invention can not be limited accordingly. That is, the equivalent changes and modifications made according to the patent scope and description content of the present invention should still be within the scope of the present invention.

INDUSTRIAL APPLICABILITY

The invention provides a multi-position double-tag adapter set for detecting gene mutation, a preparation method and a specific application thereof. The gene mutation rate of $1\times10^{-5}$ may be accurately detected, the sensitivity of gene mutation detection may be effectively improved. Combined with the throughput of high-throughput sequencing, one-time sequencing can detect multiple mutation sites of multiple genes.

The invention claimed is:

1. A multi-position double-tag adapter set for detecting gene mutation, comprising:
   a first double-tag adapter,
   a second double-tag adapter, and
   a third double-tag adapter, wherein:
      the first double-tag adapter, the second double-tag adapter, and the third double-tag adapter are respectively obtained by hybridizing an adapter primer P5 to a first adapter primer P7, a second adapter primer P7, and a third adapter primer P7,
      all 5' ends of the first adapter primer P7, the second adapter primer P7, and the third adapter primer P7 are modified with biotin,
      the adapter primer P5 is obtained by connecting SEQ ID NO:01 with a sequence shown in SEQ ID NO:02 through an I5 index sequence,
      the first adapter primer P7 is obtained by serially connecting FFFFFEEEEEJJJJJNNNNNNNNNNNN with 5' end of SEQ ID NO:03 and connecting SEQ ID NO:03 with SEQ ID NO:04 through an I7 index sequence,
      the second adapter primer P7 is obtained by serially connecting FFFFFEEEEEKKKKKNNNNNNNNNNNN with the 5' end of SEQ ID NO:03 and connecting SEQ ID NO:03 with SEQ ID NO:04 through the I7 index sequence,
      the third adapter primer P7 is obtained by serially connecting FFFFFEEEEELLLLLNNNNNNNNNNNN with the 5' end of SEQ ID NO:03 and connecting SEQ ID NO:03 with SEQ ID NO:04 through the I7 index sequence,
      the FFFFF defines protective bases for restriction sites,
      EEEEE defines the restriction sites,
      JJJJJ, KKKKK, and LLLLL define position-tag sequences,
      the JJJJJ, the KKKKK, and the LLLLL are different,
      NNNNNNNNNNNN defines a random tag sequence,
      a sequence of the I7 index sequence comprises 6 bases, and
      the NNNNNNNNNNNN comprises 4 to 12 random bases, in which no more than four continuous bases are identical.

2. The multi-position double-tag adapter set for detecting gene mutation according to claim 1, wherein:
   the NNNNNNNNNNNN is represented as BDHVBDHV,
   B represents a base other than A,
   D represents a base other than C,
   H represents a base other than G, and
   V represents a base other than T.

3. The multi-position double-tag adapter set for detecting gene mutation according to claim 1, wherein:
   the I5 index sequence is selected from SEQ ID NO:05-12,
   the I7 index sequence is selected from SEQ ID NO: 13-24,
   a sequence of the JJJJJ, the KKKKK, or the LLLLL is configured to be partially or completely overlapped with a sequence of the EEEEE, and
   when the sequence of the JJJJJ, the KKKKK, or the LLLLL is partially or completely overlapped with the sequence of the EEEEE, one or more bases of an overlapped part appear only once.

4. The multi-position double-tag adapter set for detecting gene mutation according to claim 1, wherein the FFFFF, the JJJJJ, the KKKKK, the LLLLL, and the EEEEE respectively comprise five identical bases.

5. A method for preparing the multi-position double-tag adapter set according to claim 1, comprising:
(1) after mixing the adapter primer P5, the first adapter primer P7, the second adapter primer P7, the third adapter primer P7, a buffer, and deionized water, annealing to obtain a first annealed adapter, a second annealed adapter, and a third annealed adapter;
(2) elongating the first annealed adapter, the second annealed adapter, and the third annealed adapter to obtain a first elongated adapter, a second elongated adapter, and a third elongated adapter by polymerase elongation;
(3) purifying the first elongated adapter, the second elongated adapter, and the third elongated adapter to obtain a first purified elongated adapter, a second purified elongated adapter, and a third purified elongated adapter due to ethanol precipitation or isopropanol precipitation;
(4) adding restrictive endonuclease capable of producing 3'T protruding ends into the first purified elongated adapter, the second purified elongated adapter, and the third purified elongated adapter, and performing enzyme digestion to obtain a first enzymatic digested adapter, a second enzymatic digested adapter, and a third enzymatic digested adapter;
(5) purifying the first enzymatic digested adapter, the second enzymatic digested adapter, and the third enzymatic digested adapter to obtain the first double-tag adapter, the second double-tag adapter, and the third double-tag adapter due to ethanol precipitation or isopropanol precipitation;
(6) purifying the first double-tag adapter, the second double-tag adapter, and the third double-tag adapter to obtain a product due to a biotin-avidin system; and
(7) after purifying the product to obtain the multi-position double-tag adapter set by ethanol precipitation or isopropanol precipitation.

6. A method for preparing the multi-position double-tag adapter set according to claim 2, comprising:
(1) after mixing the adapter primer P5, the first adapter primer P7, the second adapter primer P7, the third adapter primer P7, a buffer, and deionized water, annealing to obtain a first annealed adapter, a second annealed adapter, and a third annealed adapter;
(2) elongating the first annealed adapter, the second annealed adapter, and the third annealed adapter to obtain a first elongated adapter, a second elongated adapter, and a third elongated adapter by polymerase elongation;
(3) purifying the first elongated adapter, the second elongated adapter, and the third elongated adapter to obtain a first purified elongated adapter, a second purified elongated adapter, and a third purified elongated adapter due to ethanol precipitation or isopropanol precipitation;
(4) adding restrictive endonuclease capable of producing 3'T protruding ends into the first purified elongated adapter, the second purified elongated adapter, and the third purified elongated adapter, and processing enzyme digestion to obtain a first enzymatic digested adapter, a second enzymatic digested adapter, and a third enzymatic digested adapter;
(5) purifying the first enzymatic digested adapter, the second enzymatic digested adapter, and the third enzymatic digested adapter to obtain the first double-tag adapter, the second double-tag adapter, and the third double-tag adapter due to ethanol precipitation or isopropanol precipitation;
(6) purifying the first double-tag adapter, the second double-tag adapter, and the third double-tag adapter to obtain a product due to a biotin-avidin system; and
(7) after purifying the product to obtain the multi-position double-tag adapter set by ethanol precipitation or isopropanol precipitation.

7. A method for preparing the multi-position double-tag adapter set according to claim 3, comprising:
(1) after mixing the adapter primer P5, the first adapter primer P7, the second adapter primer P7, the third adapter primer P7, a buffer, and deionized water, annealing to obtain a first annealed adapter, a second annealed adapter, and a third annealed adapter;
(2) elongating the first annealed adapter, the second annealed adapter, and the third annealed adapter to obtain a first elongated adapter, a second elongated adapter, and a third elongated adapter by polymerase elongation;
(3) purifying the first elongated adapter, the second elongated adapter, and the third elongated adapter to obtain a first purified elongated adapter, a second purified elongated adapter, and a third purified elongated adapter due to ethanol precipitation or isopropanol precipitation;
(4) adding restrictive endonuclease capable of producing 3'T protruding ends into the first purified elongated adapter, the second purified elongated adapter, and the third purified elongated adapter, and processing enzyme digestion to obtain a first enzymatic digested adapter, a second enzymatic digested adapter, and a third enzymatic digested adapter;
(5) purifying the first enzymatic digested adapter, the second enzymatic digested adapter, and the third enzymatic digested adapter to obtain the first double-tag adapter, the second double-tag adapter, and the third double-tag adapter due to ethanol precipitation or isopropanol precipitation;
(6) purifying the first double-tag adapter, the second double-tag adapter, and the third double-tag adapter to obtain a product due to a biotin-avidin system; and
(7) after purifying the product to obtain the multi-position double-tag adapter set by ethanol precipitation or isopropanol precipitation.

8. A method for constructing a library, comprising:
after breaking 10 ng-1 µg of deoxyribonucleic acid (DNA) into 200-500 bp of DNA fragments:
adding terminal repair enzymes into the DNA fragments to repair terminals of the DNA fragments and adding A-tails,
adding the multi-position double-tag adapter set according to claim 1 for a connection with the DNA fragments, and
selecting 340-660 bp of fragments using Ampure magnetic beads or gel cutting after the connection is complete.

9. A method for sequencing a library, comprising:
(1) constructing the library by the method for constructing the library according to claim 8; and
(2) sequencing the library.

10. A method for analyzing a nucleic acid sequence, comprising:
(1) constructing the library by the method for constructing the library according to claim 8;
(2) sequencing a sequence of the library; and
(3) analyzing results of the sequencing,
wherein a method for the analyzing the results comprises:
   a. selecting a unique matching sequence for sequencing with a base Q value greater than 30 according to preset parameters;
   b. judging duplication according to the random tag sequence, and processing base rectifying;
   c. detecting to obtain single nucleotide polymorphisms (SNP) sites by a software; and
   d. comparing the SNP sites with mutant sites of a control group and a population genome mutation database, filtering out identical mutant sites, and defining finally remaining mutant site information as final detecting mutant site information.

11. A method for constructing a library, comprising:
after breaking 10 ng-1 μg of deoxyribonucleic acid (DNA) into 200-500 bp of DNA fragments:
   adding terminal repair enzymes into the DNA fragments to repair terminals of the DNA fragments,
   adding A-tails,
   adding the multi-position double-tag adapter set according to claim 2 for a connection with the DNA fragments, and
   selecting 340-660 bp of fragments using Ampure magnetic beads or gel cutting after the connection is complete.

12. A method for sequencing a library, comprising:
(1) constructing the library by the method for constructing the library according to claim 11; and
(2) sequencing the library.

13. A method for analyzing a nucleic acid sequence, comprising:
(1) constructing the library by the method for constructing the library according to claim 11;
(2) sequencing a sequence of the library; and
(3) analyzing results of the sequencing,
wherein a method for the analyzing the results comprises:
   a. selecting a unique matching sequence for sequencing with a base Q value greater than 30 according to preset parameters;
   b. judging duplication according to the random tag sequence, and processing base rectifying;
   c. detecting to obtain single nucleotide polymorphisms (SNP sites) by a software; and
   d. comparing the SNP sites with mutant sites of a control group and a population genome mutation database, filtering out identical mutant sites, and defining final remaining mutant site information as final detecting mutant site information.

14. A method for constructing a library, comprising:
after breaking 10 ng-1 μg of deoxyribonucleic acid (DNA) into 200-500 bp of DNA fragments:
   adding terminal repair enzymes into the DNA fragments to repair terminals of the DNA fragments,
   adding A-tails,
   adding the multi-position double-tag adapter set according to claim 3 for a connection with the DNA fragments, and
   selecting 340-660 bp of fragments using Ampure magnetic beads or gel cutting after the connection is complete.

15. A method for sequencing a library, comprising:
(1) constructing the library by the method for constructing the library according to claim 14; and
(2) sequencing the library.

16. A method for analyzing a nucleic acid sequence, comprising:
(1) constructing the library by the method for constructing the library according to claim 14;
(2) sequencing a sequence of the library; and
(3) analyzing results of the sequencing,
wherein a method for the analyzing the results comprises:
   a. selecting a unique matching sequence for sequencing with a base Q value greater than 30 according to preset parameters;
   b. judging duplication according to the random tag sequence, and processing base rectifying;
   c. detecting to obtain single nucleotide polymorphisms (SNP) sites by a software; and
   d. comparing the SNP sites with mutant sites of a control group and a population genome mutation database, filtering out identical mutant sites, and defining final remaining mutant site information as final detecting mutant site information.

\* \* \* \* \*